(12) United States Patent
Götz et al.

(10) Patent No.: US 8,203,721 B2
(45) Date of Patent: Jun. 19, 2012

(54) OPTICAL SENSOR SYSTEM ON AN APPARATUS FOR TREATING LIQUIDS

(75) Inventors: Reinhold Götz, Hamburg (DE); Kurt Harnack, Tangstedt (DE); Helmut Knofe, Norderstedt (DE); Jens-Peter Kroog, Großhansdorf (DE); Peter Scheffler, Hamburg (DE)

(73) Assignee: Eppendorf AG, Hamburg (DE)

( * ) Notice: Subject to any disclaimer, the term of this patent is extended or adjusted under 35 U.S.C. 154(b) by 616 days.

(21) Appl. No.: 12/045,411

(22) Filed: Mar. 10, 2008

(65) Prior Publication Data
US 2008/0304082 A1 Dec. 11, 2008

(30) Foreign Application Priority Data

Mar. 13, 2007 (DE) .......................... 10 2007 011 877

(51) Int. Cl.
*G01B 11/14* (2006.01)
(52) U.S. Cl. ....................................................... 356/614
(58) Field of Classification Search .................. None
See application file for complete search history.

(56) References Cited

U.S. PATENT DOCUMENTS

| | | | |
|---|---|---|---|
| 5,973,770 A | 10/1999 | Carter et al. | |
| 6,388,750 B1 | 5/2002 | Liu et al. | |
| 2003/0038950 A1* | 2/2003 | Spolaczyk | 356/624 |
| 2004/0021100 A1* | 2/2004 | Gouzman et al. | 250/573 |

FOREIGN PATENT DOCUMENTS

| | | |
|---|---|---|
| DE | 689 06 040 T2 | 10/1993 |
| DE | 197 13 362 A1 | 1/1998 |
| DE | 197 48 211 A1 | 6/1999 |
| DE | 199 24 259 A1 | 12/2000 |
| DE | 101 41 544 A1 | 3/2003 |
| EP | 1 288 635 A2 | 3/2002 |
| WO | 93/11403 | 6/1993 |
| WO | 00/42384 | 7/2000 |
| WO | 2006004987 A1 | 1/2006 |

* cited by examiner

*Primary Examiner* — Gregory J Toatley
*Assistant Examiner* — Amanda Merlino
(74) *Attorney, Agent, or Firm* — Vidas, Arrett & Steinkraus, P.A.

(57) ABSTRACT

An optical sensor system on an apparatus for treating liquids, with a device for projecting light to at least one illumination position in space, at least one device for imaging the at least one illumination position on at least one photo detector in order to supply a measurement signal depending on the received light, wherein the device for projecting is a device for simultaneously projecting light to plural illumination positions and/or the device for projecting is a device for simultaneously projecting light under different angles to the same illumination position, and/or plural photo detectors are existent, and an analysing unit connected to the at least one photo detector for analysing the at least one measurement signal.

49 Claims, 10 Drawing Sheets

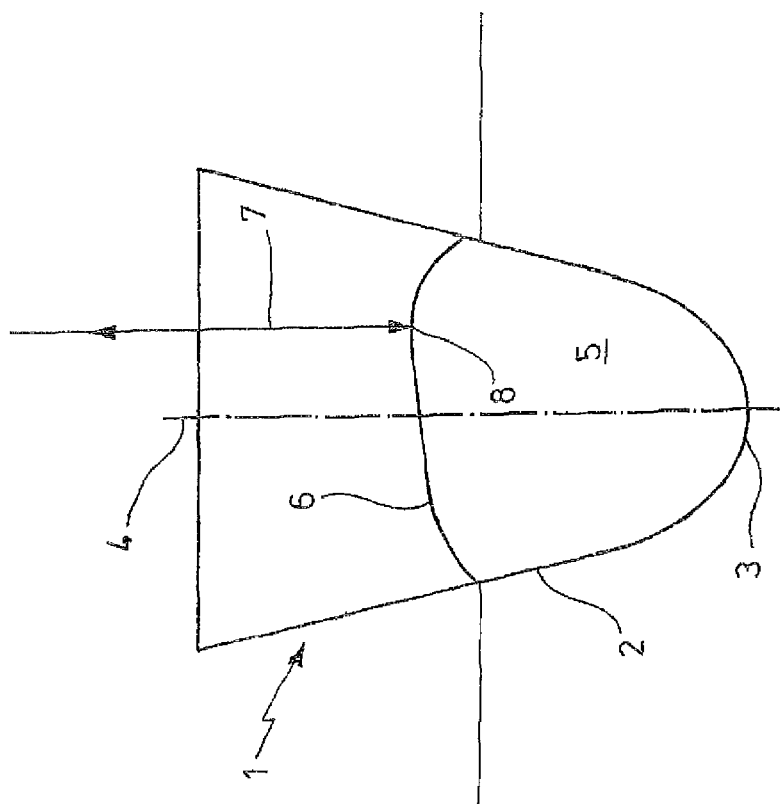
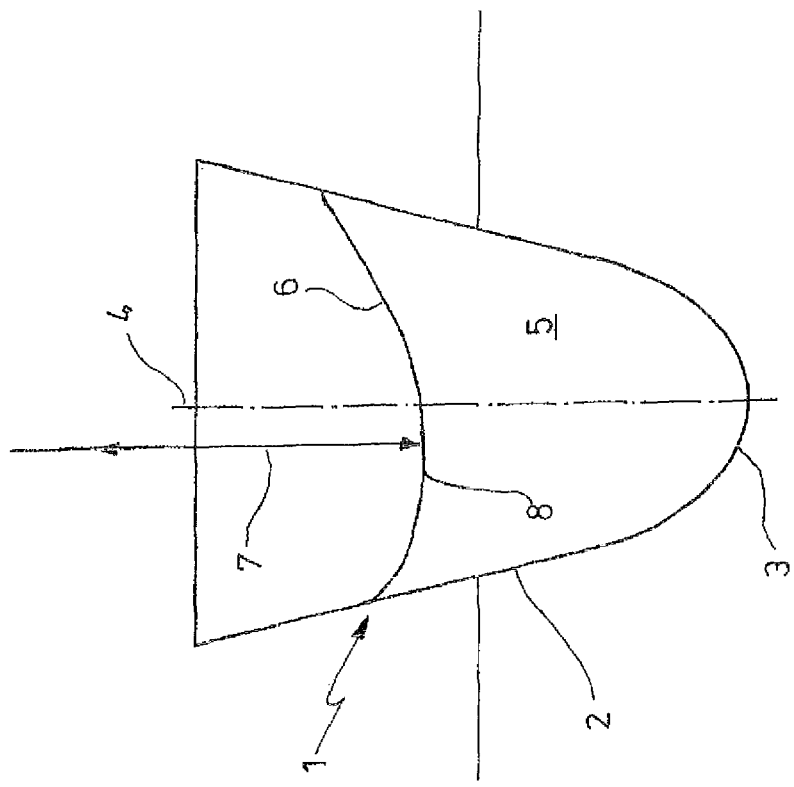

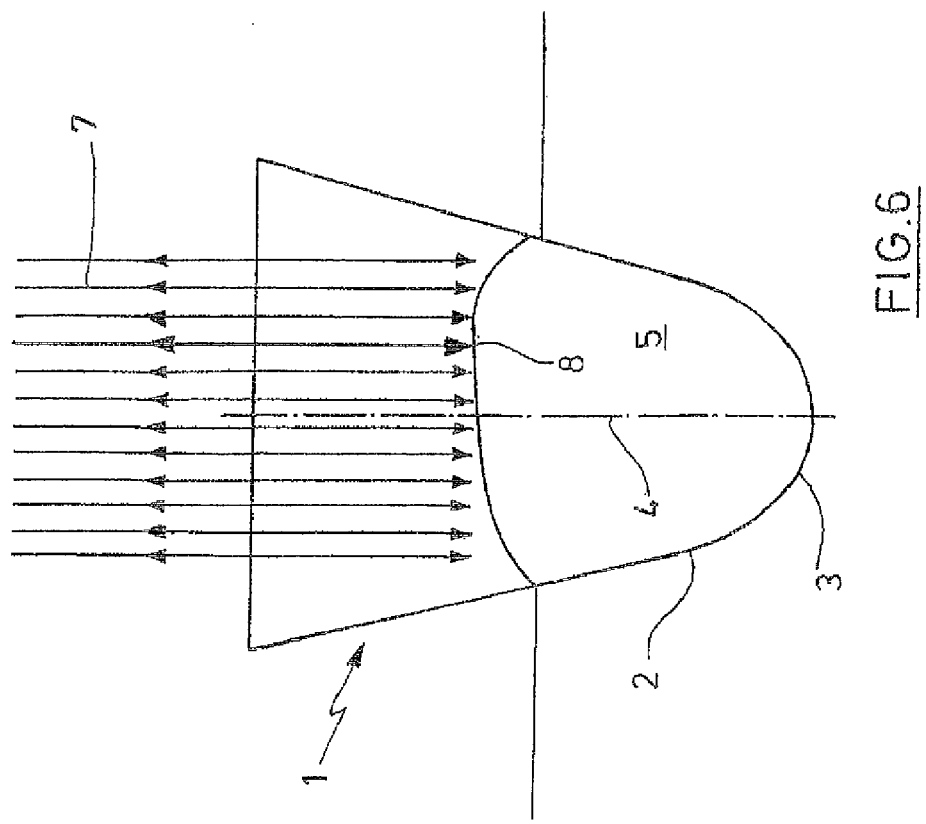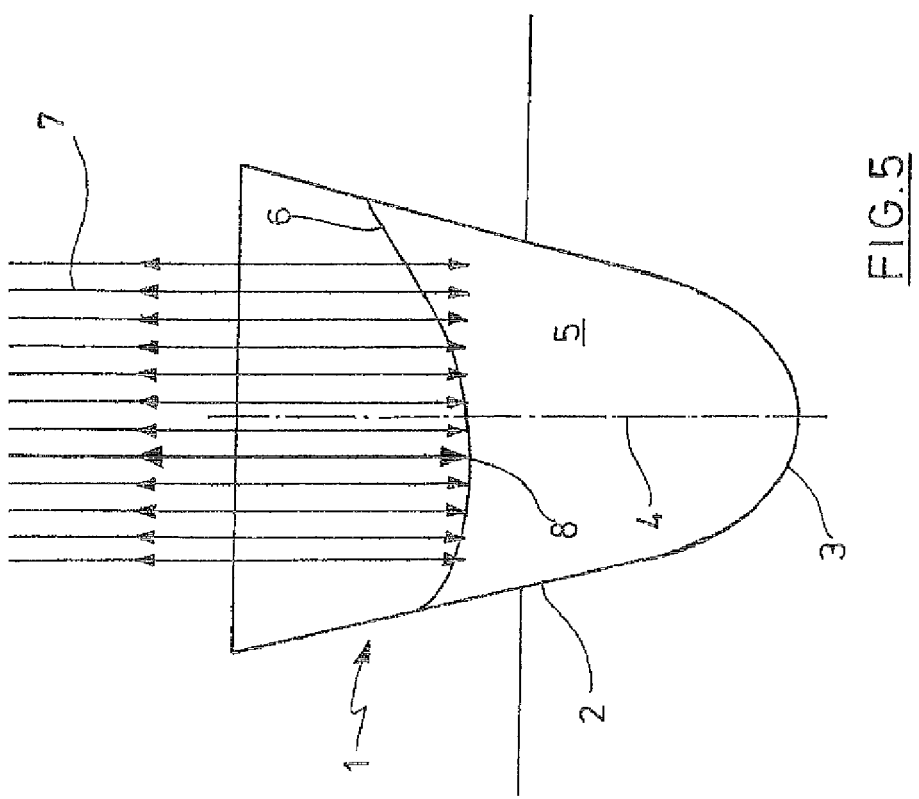

OPTICAL SENSOR SYSTEM ON AN APPARATUS FOR TREATING LIQUIDS

CROSS-REFERENCE TO RELATED APPLICATIONS

Not applicable.

STATEMENT REGARDING FEDERALLY SPONSORED RESEARCH

Not applicable.

BACKGROUND OF THE INVENTION

The present invention is related to an optical sensor system on an apparatus for treating liquids.

An optical sensor system of the type of the present invention serves for the determination of the height of a liquid level in vessels (reaction vessels or wells of microtiter plates, for instance), of the position and the identity of vessels (reaction vessels or microtiter plates, for instance) and of the position and the identity of objects (e.g. tools, accessories, pipette points in a rack and other so-called "labware" in an apparatus for treating liquids.

In particular, an apparatus for treating liquids can be an apparatus for metering and/or transporting and/or examining and/or processing (chemically, physically or biologically) liquids. In known apparatuses for treating liquids, the processes are performed either manually or partly or completely automatically. For instance, manual pipettes, PC-supported metering systems and completely automatic metering stations are known for metering. There are completely automatic treatment stations for metering, transporting, examining and processing liquids (so-called "workstations")

When pipetting manually as well as when pipetting automatically, the pipette point has to be dipped into the liquid with an immersion depth as small as possible, because the metering error increases with the immersion depth, and because the pipette point or the vessel, respectively, might be damaged upon too deep an immersion. In addition, the pipette point must be continuously submerged during the pick-up of liquid, so that no air is aspirated. In doing so, it has to be taken into account that the liquid level in the vessel decreases when picking up liquid. With manual pipettes, the user has to check the immersion depth of the pipette point continuously and to follow up with the pipette point. In automatic metering apparatuses, monitoring and control devices are used for this.

From EP 1 288 635 A2, the entire contents of which is incorporated herein by reference, an apparatus for treating liquids with an illumination device for illuminating an approximately point-shaped illumination position in space and an approximately point-shaped light receiving device with a photo detector for supplying a measurement signal depending on the intensity of the received light is known. The apparatus has an imaging system for imaging the illumination position on the approximately point-shaped light receiving device. Further, it has an analysing device for monitoring the approach of an interface between two media with different refractive indices to the illumination position, by analysing the measurement signals furnished by the photo detector. When an interface between two media with different refractive indices enters into the illumination position, the intensity of the light radiation received by the light receiving device and thus the measurement signal supplied by the photo detector changes strongly. Thus, it can be determined whether there is an interface in the illumination position or not.

Because the light beam of the illuminating device and the imaging system can be coaxially aligned towards the illumination position, touch-free retrieval of interfaces from a greater distance and with significantly less lateral space demand is possible. This promotes the retrieval of the liquid level in vessels with relatively small opening and/or relatively great depth.

It can be selectively worked with light of a wavelength for which a liquid (water e.g.) is un-transparent, in order to retrieve a liquid level free from disturbances through vessels nearby.

For the determination of the position of an interface, the relative position of illumination position and interface can be varied, until the interface is situated in the illumination position. Further, it is possible to scan the surface of an object with the illumination position, in order to deduce the position of the entire object and/or its identity based on individual values or on the course of the measurement signal. In order to do this, the apparatus may have an adjustment device for adjusting the relative position of illumination position and interface in the direction of the optical axis of the imaging system and/or transversely to it. The analysing device can trigger the adjustment of the relative position of illumination position and interface by the adjustment device. Then, the adjustment can take place depending on measurement signals, for instance in order to set the illumination position to the interface and/or to move it along the interface.

For positioning the illumination point on the interface or for finding the interface, respectively, the adjustment device must often run through long movement paths. This is very time-consuming and decreases the working speed of the apparatus for treating liquid.

Starting from this, the present invention is based on the objective to provide an optical sensor system on an apparatus for treating liquids and a method for operating such an optical sensor system which allows a more rapid detection of interfaces.

BRIEF SUMMARY OF THE INVENTION

The optical sensor system on an apparatus for treating liquids has a device for projecting light to at least one illumination position in space, at least one device for imaging the at least one illumination position on at least one photo detector in order to supply a measurement signal depending on the received light, wherein the device for projecting is a device for simultaneously projecting light to plural illumination positions and/or the device for projecting is a device for simultaneously projecting light under different angles to the same illumination position, and/or plural photo detectors are existent, and an analysing unit connected to the at least one photo detector for analysing the at least one measurement signal.

The present invention is based on the following findings in particular: The optical sensor system of the apparatus for treating liquids according to EP 1 288 635 A2, the entire contents of which is incorporated herein by reference, relies on the fact that the illuminating device, the light receiving device and the interface are aligned towards each other such that light from the illumination position on the interface is reflected accurately to the point-shaped light receiving device. When the illuminating device and the imaging system are aligned coaxially towards the illumination position, the illuminating device and the imaging system must be directed perpendicularly towards the interface, so that the light from the point-shaped illumination position is reflected to the point-shaped light receiving device. From on a certain angle of inclination of the interface with respect to the axis of the illuminating device, the reflected light no more hits the light receiving device. Thus, this inclined interface is no more detected by the optical sensor system.

In vessels, the surfaces of liquids are formed in different ways, in particular in vessels with small dimensions, like reaction vessels and deepenings of microtiter plates. The shapes of these interfaces are determined by gravitation, dimensions of the vessels, fill-in mode of the liquid, surface tension of the liquid, wetting properties of the walls of the vessels and further complex influences, which do not permit any prediction of the optimum reflexion site in which the illuminating device and the imaging system are aligned perpendicularly towards the interface.

The optimum reflexion site can be relatively great in area at planar liquid surfaces in relatively big vessels in particular, and small in area at relatively uneven liquid surfaces in small vessels in particular. Just in liquid samples pipetted by hand, the liquid surface can be inclined, because the liquid is preferably delivered on the wall of the vessel. Through this, the optimum reflexion site can be situated far off the centre.

The known optical sensor system must be moved horizontally and vertically several times, as the case might be, until the optimum reflexion site is found. Accordingly, the detection of the interface can require long movement paths and the time demand is correspondingly high.

The optical sensor system of the present invention illuminates plural illumination positions simultaneously, and/or it illuminates the same illumination position simultaneously under different angles and/or it has plural photo detectors, which can receive light simultaneously and supply a measurement signal depending on the received light. Plural illumination positions or plural photo detectors, respectively, have different positions in space. Thus, plural illumination positions can simultaneously illuminate a greater region of the interface to be detected. When an illumination position is illuminated under different angles, the light is reflected at different angles from the interface to be detected. Plural photo detectors can receive light which is emitted from the interface at different angles. In all the variants mentioned above, the probability is increased to find an optimum reflexion site in a certain arrangement of the device for projecting and of the device for imaging with respect to the interface to be detected, in which light projected to an illumination position is reflected by the interface such that it hits at least one photo detector. The same supplies a corresponding measurement signal, so that the analysing device can determine the location of the interface in the illumination position. As a consequence, it is possible that moving the optical sensor system with respect to the interface can be omitted. In as much as moving the optical sensor system with respect to the interface is necessary because an optimum reflexion site cannot be instantly located, the optical sensor system can be moved with respect to the interface until the analysing device states by analysing the measurement signals that an optimum reflexion site of the interface is in a illumination position. The movement paths for finding the optimum reflexion site can be reduced. Through this, a more rapid detection of the interface is permitted and the working speed of an apparatus for treating liquids can be enhanced.

The mentioned advantageous effects are achieved in particular when the device for projecting projects the light simultaneously to plural illumination positions and/or when it projects the light to the same illumination position under different angles simultaneously and only one single photo detector is at hand. Further, they are achieved when the device for projecting illuminates only one illumination position under only one angle and plural photo detectors are at hand. They are achieved in a particularly advantageous way when the device for projecting illuminates plural illumination positions at the same time and/or when it illuminates the same illumination position simultaneously under different angles and plural photo detectors are at hand.

The optical sensor system can detect different kinds of interfaces, liquids and objects in particular, with diffusely or directedly reflecting interfaces in particular. Thus, it may be used in particular to determine the position and/or identity of interfaces or of the liquids or objects featuring the same, respectively. In principle, the device for projecting can project the light of an extraneous light source. According to one embodiment, the device for projecting has at least one light source. According to a further embodiment, the light source is at least one laser, LED or light bulb. For instance, the laser is a semiconductor laser, a laser diode in particular.

When the device for projecting has plural light sources, the light of different light sources can be projected to different illumination positions absolutely at the same time, and/or it can be projected simultaneously to the same illumination position under different angles. However, the present invention incorporates also realisations in which the light of different light sources is projected offset in time to plural illumination positions and/or is projected offset in time to the same illumination position under different angles, so that only one light source is switched on at a certain point in time. These realisations also permit a more rapid detection of the interface, in particular when the light sources are switched on in a very rapid sequence, because by doing so the interface can be scanned much more rapidly than by displacing the known one-beam sensor system by means of the adjustment device. The consecutive switching-on of plural light sources can aid in assigning the measurement signals to the different light sources. Thus, plural light sources switched on one after the other illuminate the different illumination positions quasi simultaneously or illuminate one illumination position quasi simultaneously under different angles, and therefore they are switched on simultaneously in the spirit of the invention.

According to one embodiment, the light source emits light having a wavelength which is reflected in a particularly high degree by an interface to be detected. Accordingly, light with a wavelength other than that used for the detection of the interface of an object can be used for the detection of the interface of a liquid. When it is worked with light of a wavelength for which the liquid is un-transparent, the liquid level can be acquired free of disturbances through vessel walls nearby. When the liquid is transparent for light of a certain wavelength, the location of the vessel bottom can be detected across the liquid with this light. The suitable wavelength for the detection of a liquid can depend on the composition thereof (aqueous or organic solutions, for instance). The suitable wavelength for the detection of the surface of an object can depend on from which material (metal or plastics, e.g.), with which properties (transparent, reflecting, glossy, matte and so on) the same is made. Wavelengths in a broad range come into consideration, which includes visible and invisible light (IR- and UV-radiation). Laser diodes are at hand for the range of visible light in particular.

According to one embodiment, the device for projecting has plural separately switchable light sources with different wavelengths, which can be switched on depending on the interface to be detected. According to another embodiment, the device for projecting has one light source with adjustable wavelength (a tuneable laser diode for instance).

These embodiments permit to detect an interface with light of different wavelengths. Invalid measurement values can be recognised and discarded after check-up of the measurement with light of another wavelength. In particular, when only a very small amount of liquid is contained in a vessel, it is important to discriminate between the surface of the liquid and the bottom of the vessel. When measuring with light of only one wavelength, this may be very difficult. The use of light with different wavelengths facilitates the assignment, in particular when the wavelength is optimised according to measurement case and material.

According to one embodiment, the device for projecting is a device for projecting light to at least one point-shaped, line-shaped or two-dimensional illumination position. The point-shaped illumination position is advantageous for detecting small interfaces, of liquid levels in narrow vessels or in the wells of microtiter plates for instance. In addition, when focussing the light on at least one point-shaped illumination position, particularly strong measurement signals are obtained when a point-shaped illumination position hits an optimum reflexion site. In order to generate a point-shaped illumination position, the at least one light source is point-shaped according to one embodiment. According to a further embodiment, the device for projecting has at least one stop and/or at least one light guide in the optical path of the at least one light source, so that a quasi point-shaped light source is present at the light discharging side of the stop or the light guide, respectively.

The illumination positions may have different arrangements in space. According to embodiments, they have a three-dimensional arrangement or an arrangement in two dimensions. According to a further embodiment, the illumination positions are arranged in a convex or concave plane or in planes inclined towards each other. These embodiments approach characteristic shapes of interfaces (of liquid surfaces in narrow vessels, e.g.), and thus they can facilitate to find an optimum reflexion site.

In a three-dimensional arrangement, the illumination positions can be arranged on the intersection points of a space grid in particular. When arranged in two dimensions, they can be arranged on the intersection points of a two-dimensional grid-shaped net (or raster like, respectively) in particular, or in other patterns.

In particular, plural different illumination positions can be illumination positions separated from each other or discrete ones, respectively. Yet they may even touch each other or partially cover each other.

According to one embodiment, the light beam illuminating the at least one illumination position has an angle of aperture of 8° or below, so that the light beam can be introduced into vessels with a relatively small opening diameter and/or great depth without being shaded in the edge region. The same may be vessels with a filling volume in the milliliter range and below in particular, which are often used for the accommodation of liquids in metering stations and fully automatic treatment stations.

According to one embodiment, the distance of the illumination position from the imaging system is 100 mm or more, through which a touchless measurement of the liquid level in many usual vessels of the above-mentioned kind is possible.

The at least one illumination position can be generated in different ways. For instance, the illumination position may be illuminated by a line-shaped light beam, which can be generated by means of a laser, for instance. By at least one device for imaging, at least one point-shaped illumination position can be defined on the line-shaped light beam, which is imaged on at least one photo detector.

According to one embodiment, the device for projecting has one single light source and at least one device for imaging the light source on at least one illumination position. This device for projecting can illuminate one single illumination position in particular. For simultaneously projecting light to plural different illumination positions and/or for simultaneously projecting light to the same illumination position under different angles, according to one embodiment, the device for projecting has a device for subdividing the light source into plural virtual light sources and at least one device for imaging the plural virtual light sources to at least one illumination position.

According to one embodiment, the device for subdividing the light source has a light guide fanning out and/or a multi-hole stop. The light guide fanning itself out turns the not fanned end towards the light source and the fanned end towards the device for imaging. The virtual light sources are on the fanned end of the fanned light guide. The multi-hole stop is arranged in the light path between the light source and the device for imaging. The plural virtual light sources are defined by the stop openings of the multi-hole stop.

According to another embodiment, the device for projecting comprises plural light sources and at least one device for imaging the plural light sources on at least one illumination position. In this embodiment, the light of plural light sources is used for simultaneously projecting light to plural illumination positions and/or for simultaneously projecting light to the same illumination position under different angles.

According to a further embodiment, the device for projecting has one common device for imaging the plural virtual light sources or the plural light sources on at least one illumination position.

According to one embodiment, the at least one photo detector is point-shaped, line-shaped or planar. For instance, the at least one photo detector can be a photodiode, a photodiode array, a photodiode matrix or a planar photo detector. Preferably, the shape of the photo detector corresponds to the shape of the illumination position which is imaged on the photo detector. Thus, a point-shaped illumination position is preferably imaged on a point-shaped photo detector, a line-shaped illumination position on a line-shaped photo detector and a two-dimensional illumination position on a two-dimensional photo detector.

The photo detectors may have different arrangements in space, for instance a three-dimensional arrangement or an arrangement in a plane. The plane may be a flat plane in particular. The photo detectors can be arranged on the intersection points of a space grid or of a planar grid-shaped net (or raster-like, respectively) in particular, or in other patterns. Preferably, the arrangement of the photo detectors is corresponding to the arrangement of the illumination positions, wherein each illumination position is imaged on one of these assigned photo detectors. For instance, the illumination positions and the photo detectors are each at a time arranged on the intersection points of a space grid or of a planar grid-shaped net, the distances of the illumination positions from each other corresponding to the distances of the photo detectors from each other.

For instance, the distances of the illumination positions and/or the photo detectors are in the range of one tenth of a millimeter up to some millimeters.

In particular, the plural photo detectors can be photo detectors separated from each other or discrete ones, respectively, or they can touch each other. Plural photo detectors can be different assembly parts or parts of one single assembly part.

A point-shaped photo detector can be a photo detector with a particularly small light-sensitive area. According to one embodiment, at least one stop and/or at least one light guide is arranged in the optical path between the at least one device for imaging and the at least one photo detector. The stop or the light guide limit the passage of light to a point-shaped region of the light-sensitive area of the photo detector, so that a quasi point-shaped photo detector is obtained.

According to one embodiment, there is one single photo detector and at least one device for imaging at least one illumination position on the photo detector. Preferably, the at least one device for imaging images plural illumination positions on the single photo detector, in order to facilitate finding an optimum reflexion site. But even realisations are embraced in which the device for imaging images only one illumination position on the photo detector, to which illumination position light is projected under different angles, in order to project light to the illumination position under an angle of incidence for which the reflexion site is optimum.

According to one embodiment, a device for merging light is arranged in the optical path between the at least one device for imaging and the photo detector. The device for merging has plural inputs through which light may enter. In the device for merging, the entered light is merged and supplied to the photo detector through a common exit. According to a further embodiment, the device for merging light has light guides combining with each other.

According to one embodiment, there are plural photo detectors and at least one device for imaging at least one illumination position on the plural photo detectors. Through the plural photo detectors, the probability to receive reflected light from one single illumination position is increased. When there are plural illumination positions, the probability to receive reflected light from at least one illumination position is increased through the plural photo detectors.

According to one embodiment, the devices for projecting and the at least one device for imaging are arranged coaxially. Through this, acquisition of interfaces in narrow vessels and scanning objects with strongly structured surface is favoured.

According to one embodiment, the light of the at least one light source is supplied to the device for imaging the at least one light source on the at least one illumination position via a beam splitter, and the same device for imaging images the at least one illumination position on the at least one photo detector via the beam splitter. By doing so, a measurement of impinging light is made possible. As there is only one device for imaging, the expense is relatively small.

According to one embodiment, the at least one device for imaging the at least one light source and/or the at least one device for imaging the at least one illumination position has a tens and/or plural lenses arranged besides to each other and/or a lens array and/or a Fresnel lens. In particular, plural lenses arranged side by side transversely to the axis of the device for imaging, the lens array and the Fresnel lens are used for imaging plural light sources or virtual light sources on at least one illumination position and/or for imaging at least one illumination position on plural photo detectors.

According to one embodiment, the analysing unit has means for filtering the measurement signal supplied by the at least one photo detector. Through this, noise portions of the measurement signal can be suppressed and influences of extraneous light and other disturbances can be avoided. For instance, the measurement signals supplied by the photo detectors when moving the at least one illumination position vertically are differentiated for this purpose, and the interface is determined to be at the location where the derivative becomes zero. Further evaluation methods (for instance logarithmic, integration of higher order) for filtering out the noise signals from the measurement signal are at hand. By filtering the measurement signals, the sensitivity of the optical sensor system and the rapidity of the detection of interfaces by means of the optical sensor system is enhanced.

According to one embodiment, there is an adjustment device for adjusting the relative position of the at least one illumination position and the interface in the direction of the optical axis of the at least one imaging system and/or transversely to the same, in order to position at least one illumination position at an optimum reflexion site. According to a further embodiment, the relative position of the optics formed by the device for projecting, the imaging system and the at least one photo detector and of the interface is adjustable by means of the adjustment device. For this purpose, the optical sensor system can be shiftable, for instance by means of a horizontally and vertically (in the direction of the X-, YX- and Z-axis) movable transportation device, and/or the interface can be shiftable, by means of an object slide, for instance.

According to one embodiment, the adjustment device has a zoom lens and/or an auto focus system in the imaging system for the adjustment of the optical axis of the at least one imaging system. For the adjustment transversely to the optical axis, the adjustment device may have at least one scan minor in the imaging system.

According to one embodiment, the adjustment device is motor-driven, for instance for integration into an automatic apparatus for treating liquids.

According to one embodiment, the analysing unit triggers the adjustment of the relative position of the at least one illumination position and the interface by the adjustment device. The analysing device can perform the adjustment depending on the measurement signals, in order to set at least one illumination position to the interface and/or to move it along the interface.

According to one embodiment, the analysing unit detects the position and/or identity of interfaces or of the liquids or objects having the same, respectively. The identity of liquids or objects can be detected by scanning their interfaces with light of a specific wavelength and comparison of the measurement signals with reference data. The identity of objects can be detected by comparing the profile of the interface which was detected by scanning with reference data. The reference data can be memorised, for instance after detection through previously performed scanning of reference liquids or reference objects, respectively. The results of these determinations can be used for automatic control of processes of the apparatus for treating liquids.

According to a further embodiment, the analysing unit detects the position and/or the identity of interfaces in vessels (e.g. reaction vessels or wells of microtiter plates) and/or of laboratory goods (so-called "labware" like reaction vessels, microtiter plates, pipette points) and/or of tools.

According to one embodiment, the optical sensor system is arranged on an automatic apparatus for treating liquids.

According to one embodiment, the analysing unit is an analysing unit for acquiring an optically scannable mark of objects. The optically scannable mark is a bar code or line code arranged on an object, for instance, or an encoded arrangement of holes or of lines of a raster on the object.

The objective is resolved by a method for operating an optical sensor system where light is projected to at least one illumination position, the at least one illumination position is imaged on at least one photo detector, wherein light is projected simultaneously to plural illumination positions and/or light is projected under different angles to the same illumination position and/or the at least one illumination position is imaged on plural photo detectors, the vertical distance between the at least one illumination position and the interface is varied, the maximum value of the measurement signal of at least one photo detector is acquired when the vertical distance is varied, and the position of the illumination position at the maximum value of the measurement signal is determined as the position of the interface.

The method according to the present invention detects the spatial position of the interface in the vertical direction (or in the direction of the Z-axis, respectively), i.e. in or against the direction of the earth gravitation. A detection of the position in the horizontal direction (or the direction in the X- and Y-axis) and the assignment of the optimum reflexion site to a certain position on the interface can be omitted. Through this, the detection of the liquid level is accelerated.

According to one embodiment, in the event that no maximum value of the measurement signal of at least one photo detector is detected when the vertical distance between illumination position and interface is varied, and thereafter is searched anew for a maximum value of the measurement signal through variation of the vertical distance of the at least one illumination position and the interface, the position of the at least one illumination position is varied in the direction transverse to the vertical. These supplementary steps must be performed only when no maximum of the measurement signal is detected in the first variation of the vertical distance.

The objective is resolved by a method for operating an optical sensor system where a light in the direction of an interface is projected to at least one illumination position, the distribution of the reflected quantity of light is detected by means of plural photo detectors, and the probable position of the optimum reflexion position on the interface and/or the probable position and/or the identity of the interface is determined on the basis of the detected distribution of the quantity of light.

In this method, the probable position of the interface and/or the optimum reflexion site on the interface and/or the probable identity of the interface or the liquid having the same or the object having the same, respectively, is deduced from the distribution of the reflected light. The measurement signals supplied by plural photo detectors are analysed accordingly. The information about the probable position or the probable identity, respectively, is sufficient for many applications, for instance when it has only to be detected whether a vessel does contain any liquid or not, whether an object has reached the end of a process or whether a certain kind of objects (like a microtiter plate with 384 wells) is present. According to one embodiment, the exact determination of the position or the exact identification of the interface can be performed in an accelerated way in a postponed step, because already after analysing a few measurement signals, it can be measured in a target oriented manner. According to one embodiment, for this purpose, the at least one illumination position is adjusted towards the probable position of the optimum reflexion position or the probable position of the interface, respectively, and than the measurement is repeated.

The objective is resolved by a method for operating an optical sensor system where a light is projected to plural illumination positions, the illumination positions are moved across an interface, each illumination position is imaged on a photo detector assigned to the same, and the measurement signals supplied by the plural photo detectors are compared and a measurement error is stated in the case of a deviation.

In this method, the surface of objects is scanned several times and the measurement signals are used in order to detect measurement errors. The detection of measurement errors can be the starting point for a repeated scan of the interface of the object. Yet, a correction can also be made by using the measurement signals of further scans, which are obtained in one single working step, for the correction of an erroneous measurement. For this method, all the channels of the optical sensor system can be used, or only a part of them. It may be used in particular for scanning a bar code, a line code, an encoded arrangement of holes or of lines of a raster on an object. Yet, the method is also suited for scanning interfaces in order to identify objects.

In principle, the optical sensor system can also be used for the identification of objects or for the detection of the position thereof, respectively, when only one channel of the optical sensor system is used, i.e. by generating one single illumination position by means of one single light beam, which is imaged on one single photo detector. The multichannel optical sensor system can be switched over to a single channel optical sensor system by suitable measures, for instance by reading out only one photo detector and/or by covering illumination positions with suitable stops of the device for projecting and/or by cutting off light sources. Then, the system is capable to acquire the position of objects in space via horizontal movements (in the X- and Y-direction) of the adjustment device.

According to one embodiment, the determined positions and/or identities of interfaces and/or objects are memorised and/or are used for controlling and/or checking a method for treating liquids. The determined values can be filed in databases and can be used for the determination of liquid volumes or for the detection of the position of objects, respectively. Further, the data detected according to the method above can be provided via a bus system to a control device, which on its part controls an apparatus for treating liquids.

According to one embodiment, the positions and/or identities of interfaces and/or objects are detected in the beginning of a process for treating liquids and/or are detected anew in the course of a process for treating liquids and/or changes of the conditions through the process for treating liquids are calculated on the basis of the detected positions and/or identities. By means of a pipetting device, liquid volumes can be taken out of certain vessels and also be added thereto depending on the request of the process for treating liquids. The changes of the volumes in every vessel can be calculated and logged through a control device and can be memorised for the further steps of the process for treating liquids. In principle, a new detection of the position of interfaces of liquids is then no more necessary. Further, objects can be moved according to the method for treating liquids via a gripping- or other transporting device. Even in this, it is in principle not necessary to detect the new position or the absence of objects at a certain location, because the new position can be calculated. Thus, in principle it is sufficient to detect the conditions (locations and/or identities of interfaces or of the liquids or objects featuring the same, respectively) in the beginning of the process for treating liquids, lest they are preset by the user.

According to a further embodiment, the calculated values are checked by a new detection of the positions and/or identities. In each intermediate stage of the method for treating liquids, the commands and actions performed before can be examined and the values at this intermediate stage can be memorised.

According to a further embodiment, the detected and/or calculated positions and/or identities are filed and/or displayed. After completion of a process, examination of all the performed commands or actions, respectively, is possible by means of the optical sensor for purposes of quality management or validation, respectively. The results can be memorised and/or output for filing and/or verification.

BRIEF DESCRIPTION OF THE SEVERAL VIEWS OF THE DRAWINGS

In the following, the present invention is explained in more detail by reference to the attached drawings of examples of its realisation. In the drawings show:

FIG. 1 a light beam at an optimum reflexion site of a concavely curved interface of a liquid in a vessel, in a vertical section;

FIG. 2 a light beam at an optimum reflexion site of a convexly curved interface of a liquid in a vessel, in a vertical section;

FIG. 5 plural parallel light beams at a concavely curved interface of a liquid in a vessel, in a vertical section;

FIG. 6 plural parallel light beams at a convexly curved interface of a liquid in a vessel, in a vertical section;

DETAILED DESCRIPTION OF THE INVENTION

Figure 3:
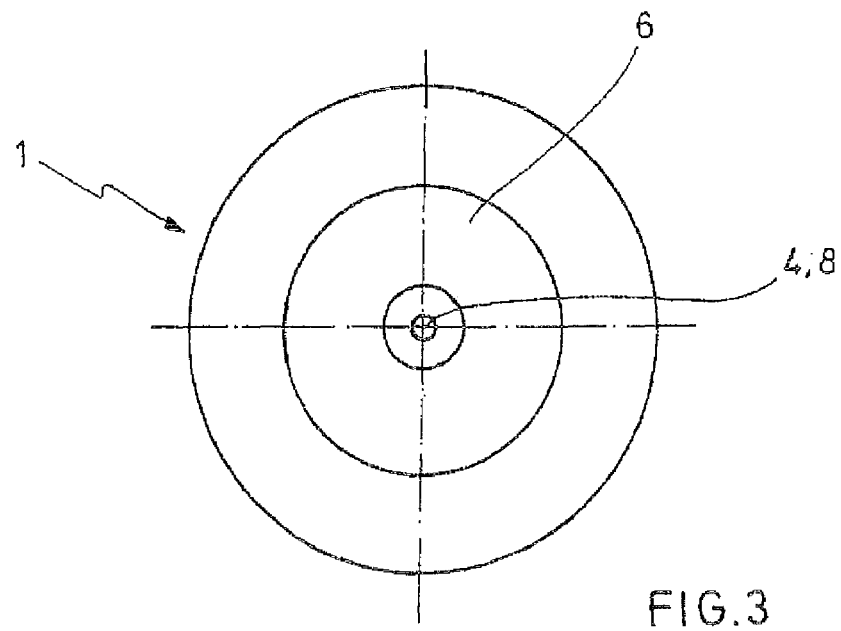
FIG. 3 the position of an ideal reflexion site of the interface of a liquid in a vessel in a top view.

While this invention may be embodied in many different forms, there are described in detail herein a specific preferred embodiment of the invention. This description is an exemplification of the principles of the invention and is not intended to limit the invention to the particular embodiment illustrated.

In the following description, coincident parts of different realisation examples are designated with the same reference numerals.

FIG. 1 to 7 show examples for the generation of the liquid level in a reaction vessel with a capacity in the range of a fraction of a milliliter up to some milliliters. Such reaction vessels are marketed by the applicant under the designation of "Eppendorf Röhrchen" or "Eppendorf tubes", respectively.

The vessels 1 are conical in the lower part 2 and have a vessel bottom 3 concavely domed at the inside. The vessels 1 are aligned vertically with their axis 4.

According to FIG. 1, a liquid 5 arranged in the vessel 1 has a concavely curved "meniscus" or interface 6.

A light beam 7, directed parallel to the vessel axis 4 towards the interface 6, hits the interface 6 vertically at an optimum reflexion site 8. From the optimum reflexion site 8, it is reflected parallel to the vessel axis 4. An apparatus for acquiring interfaces according to FIG. 1 of EP 1 288 635 A2 can acquire the position of the interface 6 when the light beam is directed to the optimum reflexion site 8.

FIG. 2 shows the optimum reflexion site 8 on a convexly curved interface 6 in the vessel 1.

According to FIG. 3, the optimum reflexion site 8 is arranged on the central axis 4 of the vessel 1 in the ideal case. When the position of the vessel 1 is known, the fill level can be determined easily by means of the apparatus for acquiring interfaces according to EP 1 288 635 A2. According to FIG. 4, the optimum reflexion site 8 is arranged off-centre in reality. A sensor system according to EP 1 288 635 A2 must be moved vertically and horizontally in order to find the optimum reflexion site 8.

According to the present invention, plural parallel light beams 7 are directed towards the interface 6 in the vessel 1 according to FIGS. 5 and 6. One of the parallel light beams 7 at a time hits the optimum reflexion site 8. Thus, the reflected light can be detected by means of a not shown photo detector, which is directed towards the reflected light.

Figure 4:
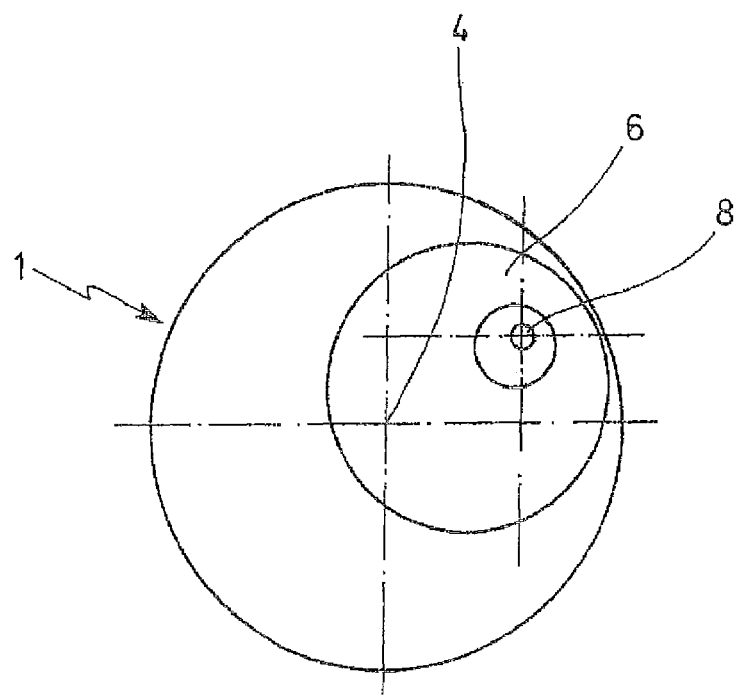
FIG. 4 the position of a real reflexion site of the interface of a liquid in a vessel in a top view.
Figure 7:
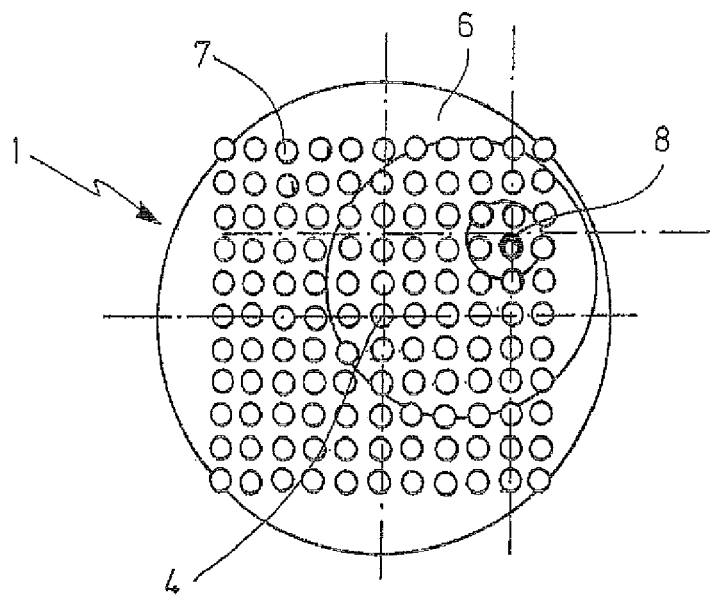
FIG. 7 scanning the real interface of a liquid in a vessel by means of plural matrix-like arranged light beams, in a top view.

FIG. 7 illustrates how the optimum reflexion site 8 is found by means of a matrix-like arrangement of light beams 7 on a real interface 6 corresponding to FIG. 4. In principle, the optimum reflexion site 8 can be found in one single scanning process. As the case may be, a device for projecting the light beams 7 must be moved in the vertical (perpendicular to the drawing plane) in order to focus a light beam 7 at the optimum reflexion site 8 on the interface 6.

Figure 8:
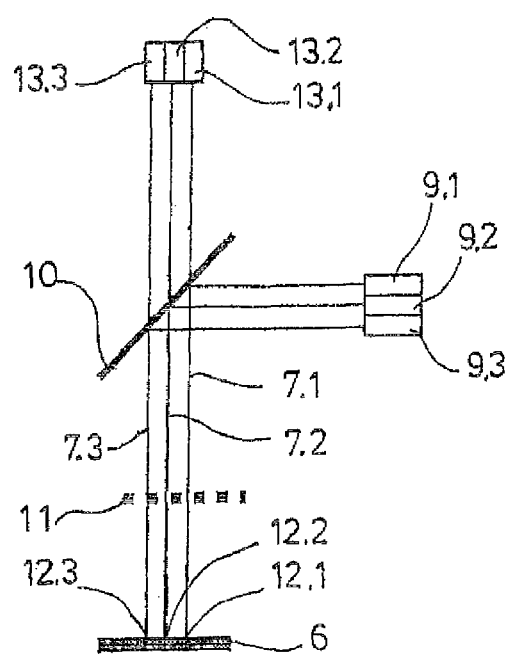
FIG. 8 optical sensor system with plural light sources and plural photo detectors, in a schematic side view.

Plural light beams 7 for scanning the interface 6 can be generated in different ways. In the following, some examples for this are explained:

According to FIG. 8, parallel light beams 7.1, 7.2, 7.3 from parallel light sources 9.1, 9.2, 9.3 are directed towards a beam splitter 10. From the beam splitter 10, the light beams 7.1, 7.2, 7.3 are reflected to a lens array 11. The lens array 11 has a plurality of lenses arranged side by side, wherein one lens is assigned to each light beam 7.1, 7.2, and 7.3 at a time. Through the lens array 11, the light beams 7.1, 7.2, 7.3 are focussed on raster-like arranged illumination positions 12.1, 12.2, 12.3.

In the example, all the light beams 7.1, 7.2, 7.3 hit a reflecting interface 6 perpendicularly, so that the light is reflected in the direction of the incident light beams 7.1, 7.2, 7.3. The reflected light is imaged on parallel photo detectors 13.1, 13.2, 13.3 by the lens array 11 and the beam splitter 10.

The lens array 11 focuses the light beams 7.1, 7.2, 7.3 on illumination positions 12.1, 12.2, 12.3, and the light reflected from the illumination positions on the photo detectors 13.1, 13.2, and 13.3. When the illumination positions 12.1, 12.2, 12.3 are on the interface 6, the amount of light received by the photo detectors 13.1, 13.2, 13.3 is maximum. Thus, the measurement signals of the photo detectors 13.1, 13.2, 13.3 indicate that the illumination positions 12.1, 12.2, 12.3 are on the interface 6. Through this, the distance of the interface 6 from the optical sensor system is known.

In FIG. 8, the interface 6 is even. With an uneven interface 6, only a light beam 7.1 or 7.2 or 7.3 perpendicularly incident to a region of this interface hits the optimum reflexion site 8. The reflected light is received by photo detector 13.1 or 13.2 or 13.3, on which the corresponding illumination position 12.1 or 12.2 or 12.3 is imaged. The measurement signal of photo detector 13.1 or 13.2 or 13.3 indicates that the optimum reflexion site 8 is found, so that the distance of the interface 6 from the optical sensor system can be determined on a non-planar interface 6.

Figure 9:
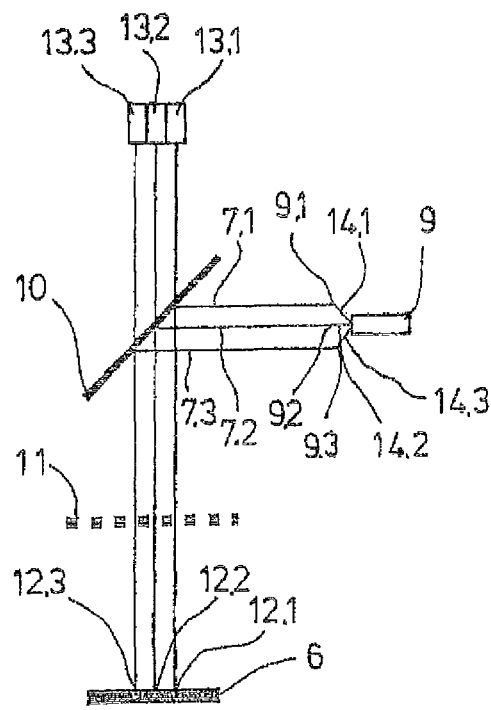
FIG. 9 optical sensor system with plural virtual light sources and plural photo detectors, in a schematic side view.

The optical sensor system of FIG. 9 has only one single light source 9. The light of this light source is subdivided into plural virtual light sources 9.1, 9.2, 9.3 by a light guide 14.1, 14.2, 14.3 fanning itself. The light beams 7.1, 7.2, 7.3 departing from this are in turn focussed on illumination positions 12.1, 12.2, 12.3 via an arrangement of beam splitter 10 and lens array 11, in the manner which is already described. The light beams reflected from optimum illumination positions are imaged on parallel photo detectors 13.1, 13.2, 13.3.

Figure 10:
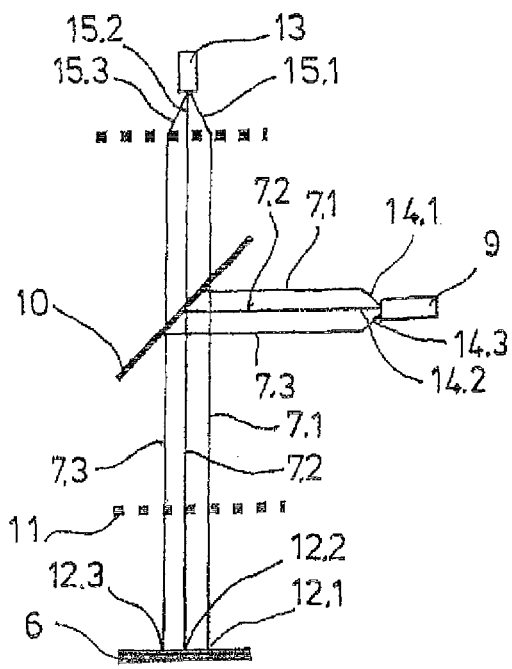
FIG. 10 optical sensor system with plural virtual light sources and one photo detector with light combination at the upstream side, in a schematic side view.

The optical sensor system from FIG. 10 differs from that one described previously in that it has only one photo detector 12. Upstream to the photo detector 12 there are light guides 15.1, 15.2, and 15.3, which combine with each other or fuse together, respectively. The fanned ends of the light guides 15.1, 15.2, 15.3 are each at a time assigned to one light beam 7.1, 7.2, 7.3. The light reflected from the illumination positions 12.1, 12.2, 12.3 in the direction of the incident light beams 7.1, 7.2, 7.3 is imaged on the entrances of the light guides 15.1, 15.2, 15.3. The light arriving there is supplied to the photo detector 13 in a bunched form. The arrangement of an optimum reflection site 8 of the interface 6 in at least one illumination position 12.1, 12.2, 12.3 is evidenced in an enhanced measurement signal of the photo detector 13.

Figure 11:
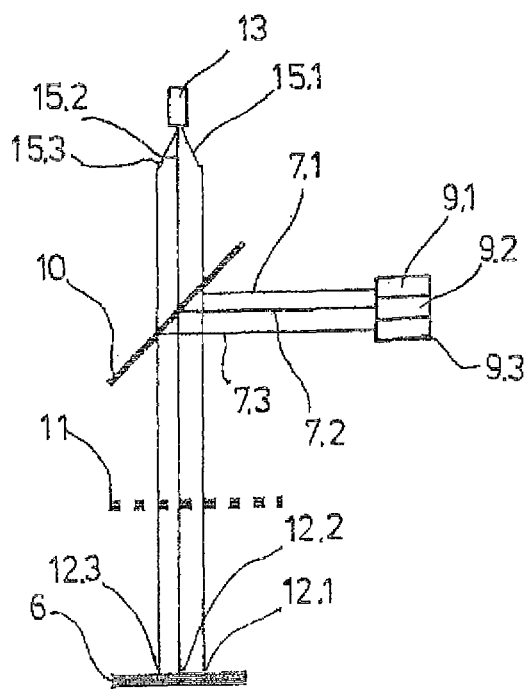
FIG. 11 optical sensor system with plural light sources and one photo detector with light combination at the upstream side, in a schematic side view.

The optical sensor system according to FIG. 11 combines the plural light sources 9.1, 9.2, 9.3 of the optical sensor system of FIG. 8 with combining light guides 15.1, 15.2, 15.3 and a downstream situated photo detector 13 of FIG. 10. Thus, the virtual light sources of FIG. 10 are substituted through real light sources 9.1, 9.2, 9.3. When at least one illumination position 12.1, 12.2, 12.3 hits an optimum reflexion site 8 of an interface 6, this is evidenced in an increase of the measurement signal supplied by the photo detector 13.

Figure 12:
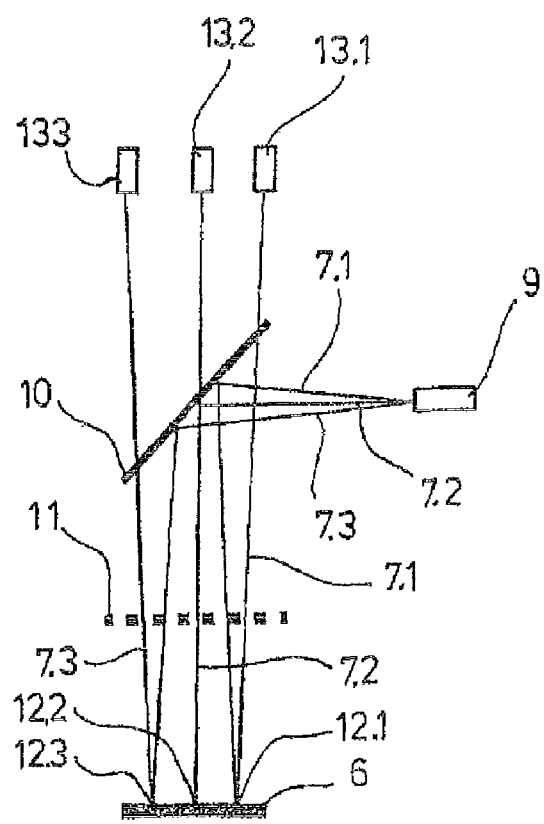
FIG. 12 optical sensor system with one light source with diverging light beams and plural photo detectors with convergent alignment, in a schematic side view.

In the arrangement of FIG. 12, a light source 9 supplies diverging light beams 7.1, 7.2, 7.3, which are reflected by the beam splitter 10 and focussed on illumination positions 12.1, 12.2, 12.3 via a lens array 11. All the illumination positions 12.1, 12.2, 12.3 hit a planar interface 6. The light beams 7.1, 7.2, 7.3 reflected from there are imaged on photo detectors 13.1, 13.2, 13.3 via the lens array 11 and the beam splitter 10. When only a part of the interface 6 is even, only the light beam 7.1 or 7.2 or 7.3 incident there is reflected towards the assigned photo detector 13.1, 13.2, 13.3. As a consequence, from the increase of the measurement signal of at least one photo detector 13.1, 13.2, 13.3 it can be recognised that the interface 6 is situated in an illumination position 12.1, 12.2, and 12.3.

Figure 13:
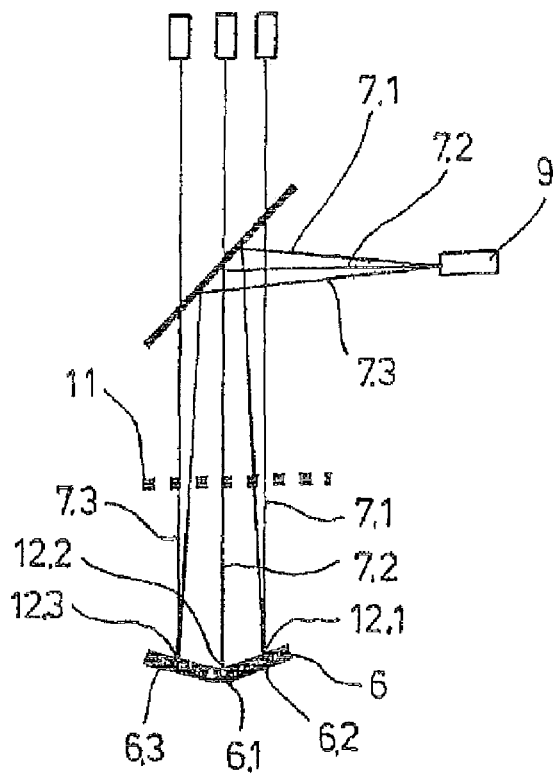
FIG. 13 optical sensor system with diverging light beams directed to inclined interfaces and plural parallel photo detectors, in a schematic side view.

The realisation of FIG. 13 differs from that one described above in that all the photo detectors 13.1, 13.2, 13.3 are situated on light beams 7.1, 7.2, 7.3, which are parallel reflected by an interface 6. Because the light source 9 emits diverging light beams 7.1, 7.2, 7.3, they are reflected to the assigned photo detectors 13.1, 13.2, 13.3 only by an interface 6 with a planar central region 6.1 and two oppositely inclined edge regions 6.2, 6.3. The shape of the interface 6 corresponds about to the form of a concave meniscus, which is often formed by the surface of a liquid in a vessel. This arrangement is therefore particularly suited for the detection of liquid levels in vessels. Through the increase of the sums of the measurement signals of the photo detectors 13.1, 13.2, 13.3, the arrangement of the illumination positions 12.1, 12.2, 12.3 on the interface 6.1, 6.2, 6.3 is particularly well recognisable.

Figure 14:
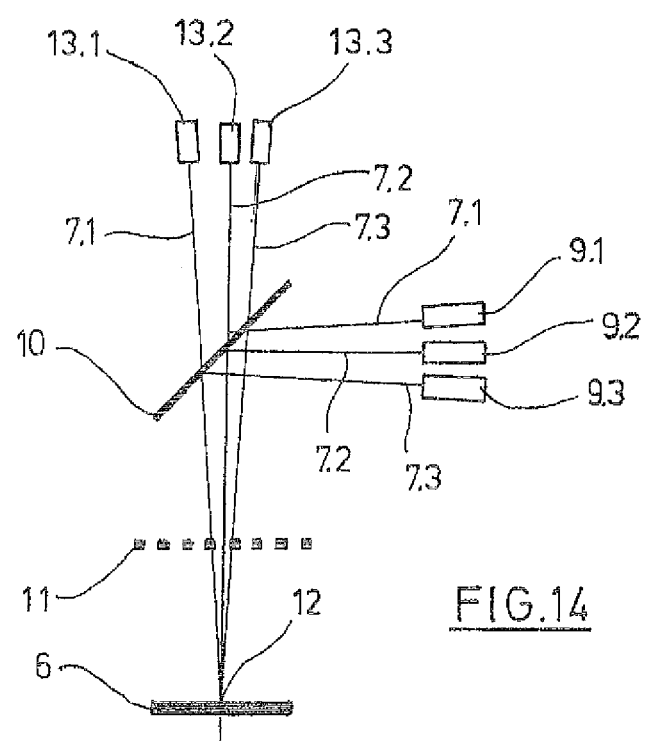
FIG. 14 optical sensor system with plural light sources with light beams directed to one common illumination point under different angles, and plural photo detectors aligned towards them, in a schematic side view.

The optical sensor system of FIG. 14 has light sources 9.1, 9.2, 9.3, whose light beams 7.1, 7.2, 7.3 converge such that they meet each other in a common illumination position 12 after reflection by a beam splitter 10 and bunching by a lens array 11. Photo detectors 13.1, 13.2, 13.3 are arranged on the light beams 7.1, 7.2, 7.3, which are reflected by a planar interface 8 which is aligned perpendicular to the axis of the lens array 11. The arrangement of an optimum reflection site in the illumination position is evidenced by the increase of the measurement signals of all the photo detectors 13.1, 13.2, 13.3. If only one of the incident light beams 7.1 or 7.2 or 7.3 is reflected on a photo detector 13.1 or 13.2 or 13.3, this is shown by an increase of the measurement signal of the corresponding photo detector. Therefore, even this optical sensor system facilitates to find an optimum reflexion site.

When the illumination positions 12.1, 12.2, 12.3 of the optical sensor system described above do not hit an optimum reflexion site 8 of an interface 6, by displacing the optical sensor system with respect to the interface 6 it can be obtained that one illumination position hits an optimum reflexion site 8, and thus the position of the interface 6 can be determined.

Figure 15:
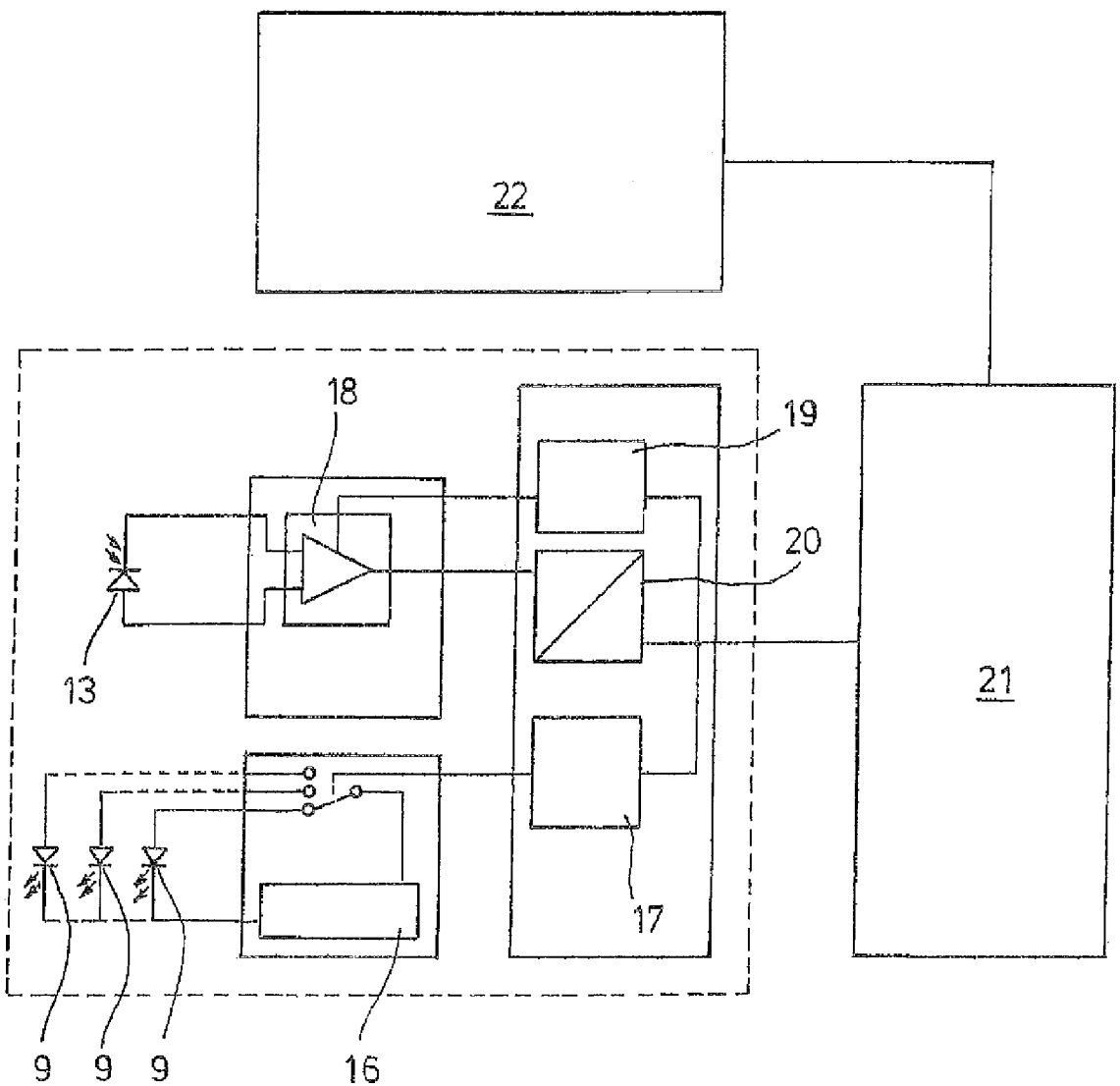
FIG. 15 block diagram of an optical sensor system according to FIG. 10.

According to FIG. 15, an optical sensor system has a power supply 16 for plural light sources 9 which have different wavelengths. The light sources 9 are controlled by a light control device 17. By means of the light control device 17, one of the different light sources 9 can be selectively switched on, wherein the best wavelength for the detection of a certain interface can be selected.

The measurement signal of a photo detector 13 is supplied to a noise filter 20 via an amplifier 18 with amplification control 19. After digitalisation by means of a not shown A/D-converter, the filtered measurement signal is supplied to an analysing device in the form of a computer 21, which analyses the measurement signals. Depending on the measurement signals, the computer 21 triggers an adjustment device 22 for adjusting the optical sensor system with respect to an interface in the horizontal (X-Y) and vertical (Z-) direction.

Figure 16:
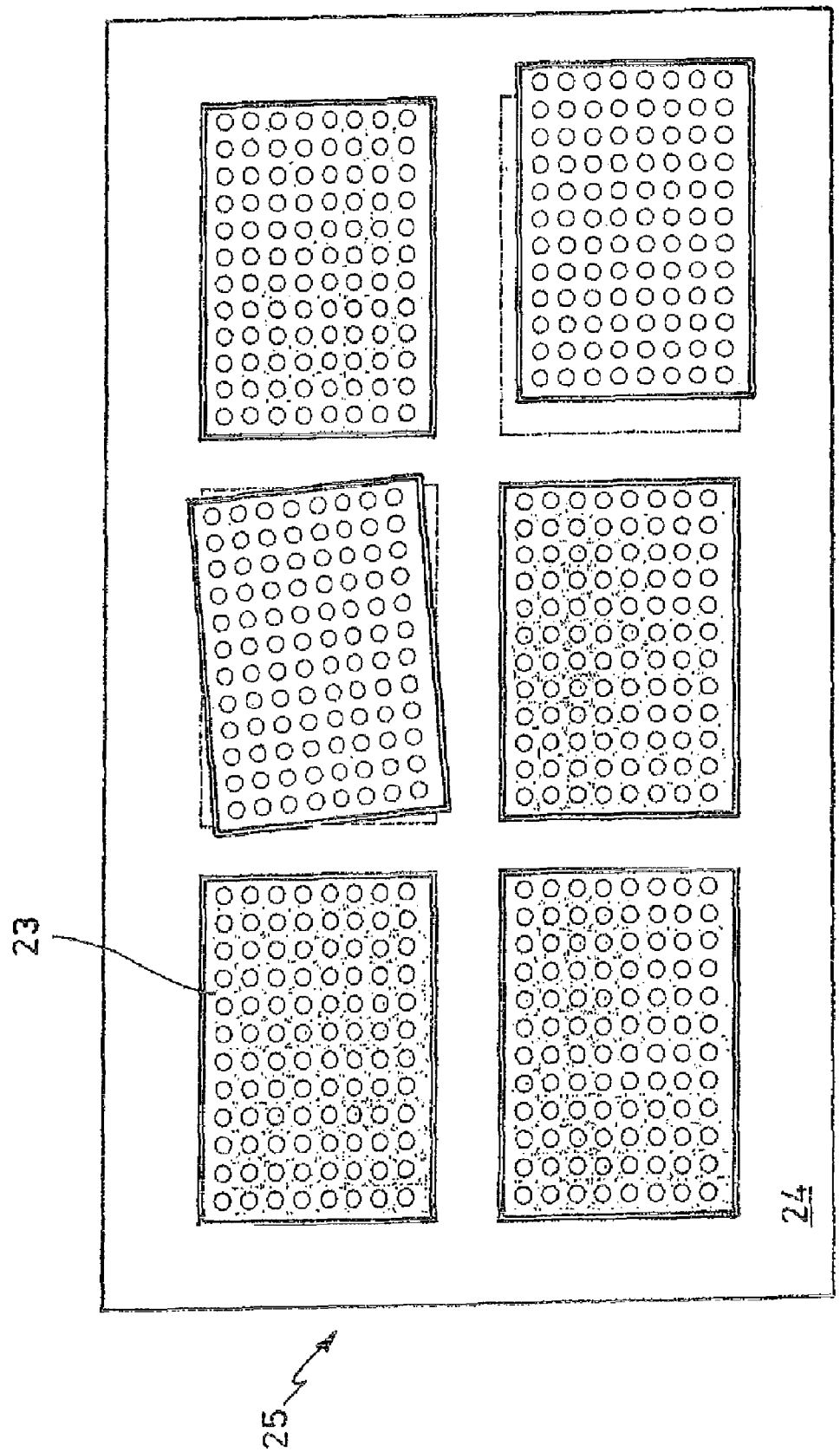
FIG. 16 exemplary arrangement of microtiter plates in an apparatus for treating liquids with an optical sensor system, in particular for position recognition and identification of labwares, in a top view.

According to FIG. 16, an optical sensor system according to the present invention can determine the position of microtiter plates 23 in the working area 24 of an apparatus for treating liquids 25. A swiveling, a parallel shift or another erroneous arrangement of a microtiter plate 23 with respect to an intended position is recognised with the aid of the optical sensor system. It can be corrected or taken into account, respectively, in the treatment of liquids in the wells of the microtiter plates 23 and/or in a transportation of the microtiter plates 23.

Figure 17:
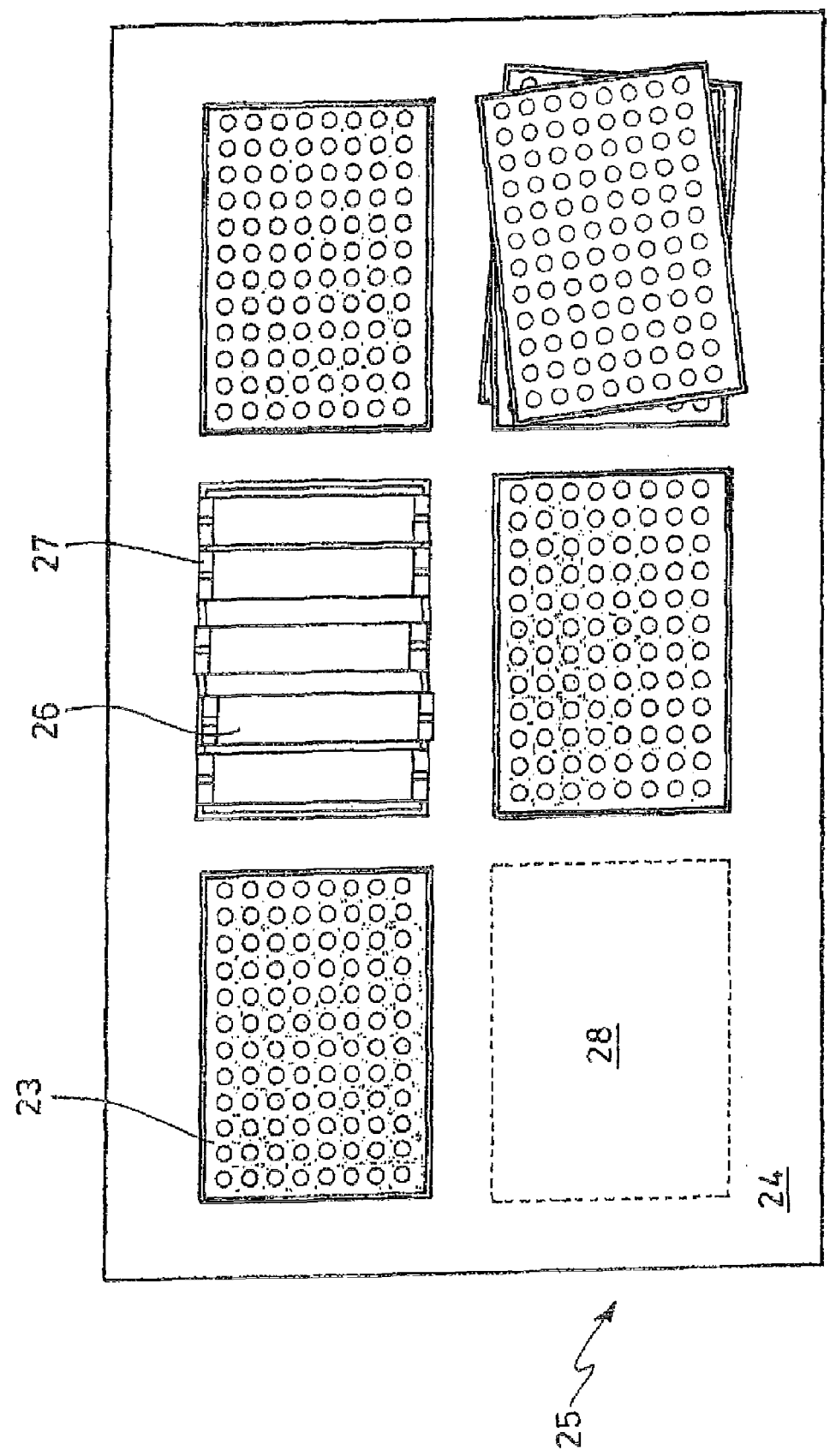
FIG. 17 exemplary arrangement of labwares in an apparatus for treating liquids with an optical sensor system, in particular for position recognition and identification of labwares, in a top view.

According to FIG. 17, the position of microtiter plates 23 and receiver vessels 26 in a rack 27 and the absence of a microtiter plate on a position 28 intended for the same can be determined with the aid of an optical sensor system. The detected condition of the labwares in the working area 24 of the apparatus for treating liquids 25 is taken into account in the further treatment steps.

Figure 18:
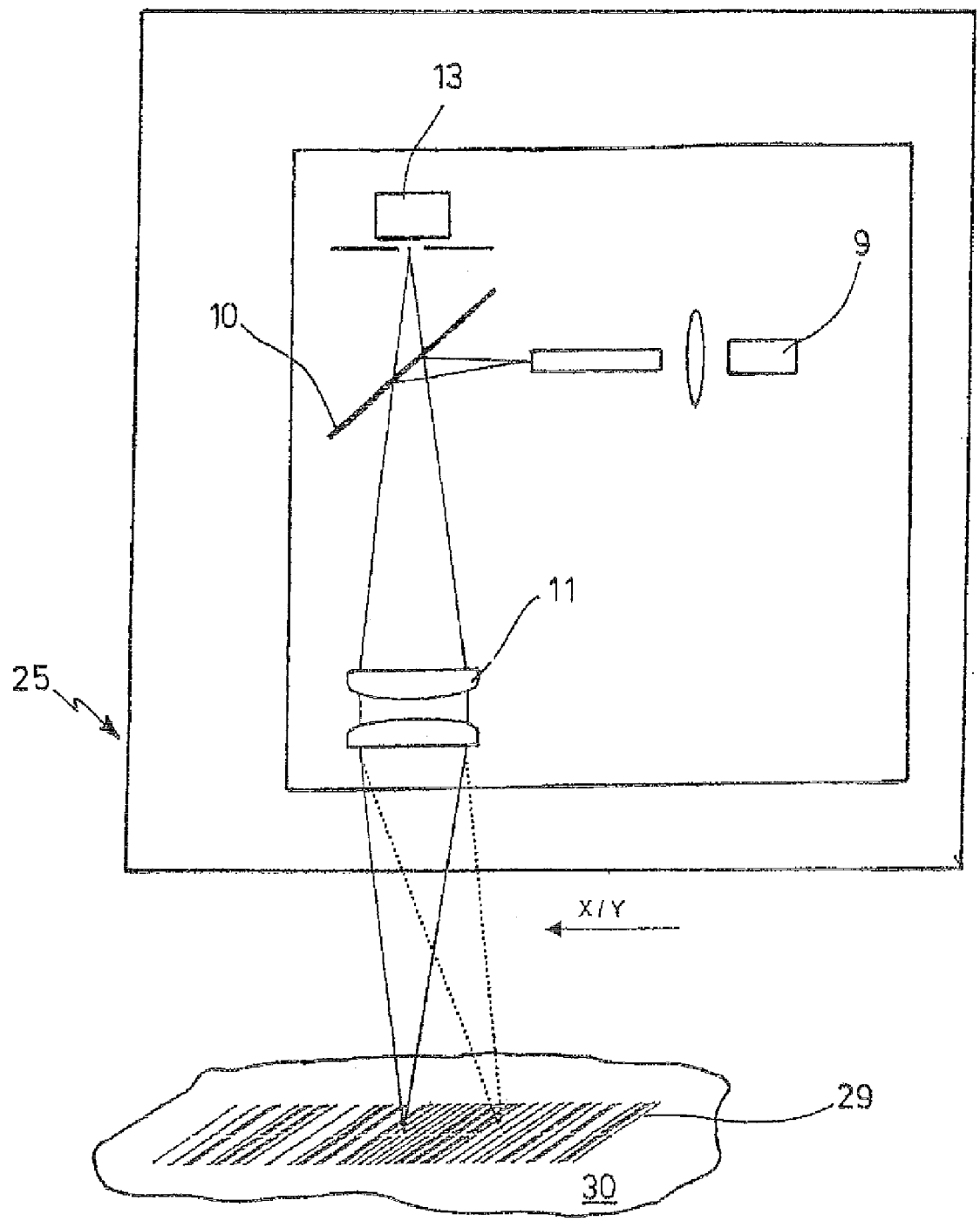
FIG. 18 optical sensor system when it scans a bar code, in a schematic side view.

FIG. 18 shows an optical sensor system in which only one light source 9 and only one photo detector 13 is switched on for scanning a bar code, so that the measurement arrangement corresponds to the realisation example according to EP 1 288 635 A2. The explanations related to this in the German specification laid open to public inspection mentioned above are incorporated by reference into the present application. By means of the measurement arrangement, a bar code 29 on an object 30 is scanned in order to identify the same. For checking the scan, a simultaneous measurement can be performed by activating a—not shown—second light source 9 and a—not shown—second photo detector. For this purpose, the optical sensor system is moved in the horizontal direction with respect to the bar code 29.

The above disclosure is intended to be illustrative and not exhaustive. This description will suggest many variations and alternatives to one of ordinary skill in this art. All these alternatives and variations are intended to be included within the scope of the claims where the term "comprising" means "including but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

What is claimed is:

1. An optical sensor system for a touchless measurement on an apparatus for treating liquids, with a device for projecting light (9, 10, 11) to plural illumination positions (12) in space, at least one device for imaging (11) the plural illumination positions reflected by the surface of the liquid on at least one photo detector (13) in order to supply at least one measurement signal depending on the received light, wherein the device for projecting (9, 10, 11) is a device for simultaneously projecting light to plural illumination positions arranged in a flat or convex or concave plane or in planes inclined towards each other approaching the characteristic shapes of liquid surfaces in narrow vessels.

2. An optical sensor system according to claim 1, wherein the device for projecting (9, 10, 11) has at least one light source (9).

3. An optical sensor system according to claim 2, wherein the at least one light source (9) is at least one laser, LED or light bulb.

4. An optical sensor system according to claim 2, wherein the at least one light source (9) emits light having a wavelength which is reflected in a particularly high degree by an interface (6) which is to be detected.

5. An optical sensor system according to claim 1, wherein the device for projecting (9, 10, 11) has plural separately switchable light sources (9) with different wavelengths and/or has one light source (9) with adjustable wavelength.

6. An optical sensor system according to claim 1, wherein the device for projecting (9, 10, 11) is a device for projecting light to at least one point-shaped, line-shaped or two-dimensional illumination position (12).

7. An optical sensor system according to claim 2, wherein the at least one light source (9) is point-shaped.

8. An optical sensor system according to claim 7, wherein the device for projecting (9, 10, 11) has at least one stop and/or at least one light guide (14) in the optical path of the at least one light source (9).

9. An optical sensor system according to claim 1, wherein the illumination positions (12) have a three-dimensional arrangement or an arrangement in a plane.

10. An optical sensor system according to claim 9, wherein the illumination positions (12) are arranged in a plane.

11. An optical sensor system according to claim 1, wherein the illumination positions are arranged in a convex or concave plane or in planes inclined towards each other.

12. An optical sensor system according to claim 1, wherein a light beam (7) illuminating the at least one illumination position (12) has an angle of aperture of 8° or below.

13. An optical sensor system according to claim 1, wherein the distance of the at least one illumination position (12) from the device for projecting (9, 10, 11) is 100 mm or more.

14. An optical sensor system according to claim 1, wherein the device for projecting (9, 10, 11) has one single light source (9) and at least one device for imaging (11) the light source on at least one illumination position (12).

15. An optical sensor system according to claim 14, wherein the device for projecting (9, 10, 11) has a device for subdividing (14) the light source into plural virtual light sources, and at least one device for imaging (11) the plural virtual light sources to at least one illumination position (12).

16. An optical sensor system according to claim 15, wherein the device for subdividing (14) the light source (9) has a light guide fanning out and/or a multi-hole stop.

17. An optical sensor system according to claim 2, wherein the device for projecting (9, 10, 11) has plural light sources (9) and at least one device for imaging (11) the plural light sources on at least one illumination position (12).

18. An optical sensor system according to claim 15, wherein the device for projecting (9, 10, 11) has one common device for imaging (11) the plural virtual light sources or the plural light sources on at least one illumination position (12).

19. An optical sensor system according to claim 1, wherein the at least one photo detector (13) is point-shaped, line-shaped or two-dimensional.

20. An optical sensor system according to claim 19, wherein at least one stop and/or at least one light guide (15) is arranged in the optical path between the at least one device for imaging (11) and the at least one photo detector (13).

21. An optical sensor system according to claim 1, with one single photo detector (13) and at least one device for imaging (11) at least one illumination position (12) on the photo detector (13).

22. An optical sensor system according to claim 21, wherein a device for merging (15) light is arranged in the optical path between the at least one device for imaging (11) and the photo detector (13).

23. An optical sensor system according to claim 22, wherein the device for merging (15) light has light guides combining with each other.

24. An optical sensor system according to claim 1, with plural photo detectors (13) and at least one device for imaging (11) at least one illumination position (12) on the plural photo detectors (13).

25. An optical sensor system according to claim 1, wherein the device for projecting (9, 10, 11) and the at least one device for imaging (11) are arranged coaxially.

26. An optical sensor system according to claim 1, wherein the light of the at least one light source (9) is supplied to the device for imaging (11) at least one light source on the at least one illumination position (12) via a beam splitter (10), and the same device for imaging (11) images the at least one illumination position (12) on the at least one photo detector (13) via the beam splitter (10).

27. An optical sensor system according to claim 1, wherein the at least one device for imaging (11) at least one light source (9) and/or the at least one device for imaging (11) or the at least one illumination position (12) has a lens and/or plural lenses arranged side by side and/or a lens array and/or a Fresnel lens.

28. An optical sensor system according to claim 1, wherein the analysing unit (21) has means for filtering (20) the measurement signal supplied by the at least one photo detector (13).

29. An optical sensor system according to claim 1, with an adjustment device (22) for adjusting the relative position of the at least one illumination position (12) and the interface (6) in the direction of the optical axis of the at least one imaging system (11) and/or transversely to the same.

30. An optical sensor system according to claim 29, wherein the relative position of the optics formed by the device for projecting (9, 10, 11), the imaging system (11) and the at least one photo detector (13) and of the interface (6) is adjustable by means of the adjustment device (22).

31. An optical sensor system according to claim 29, wherein the adjustment device (22) has a zoom lens and/or an auto focus system in the imaging system.

32. An optical sensor system according to claim 29, wherein the adjustment device (22) is motor-driven.

33. An optical sensor system according to claim 29, wherein the analysing unit (21) triggers the adjustment of the relative position of the at least one illumination position (12) and the interface (6) by the adjustment device (22).

34. An optical sensor system according to claim 1, wherein the position and/or identity of interfaces is determined by the analysing unit (21).

35. An optical sensor system according to claim 34, wherein the analysing unit (21) determines the position and/or the identity of interfaces in vessels and/or of laboratory goods and/or of tools.

36. An optical sensor system according to claim 1 on an automatic apparatus for treating (25) liquids.

37. An optical sensor system according to claim 1, wherein the analysing unit (21) is an analysing unit for acquiring an optically scannable mark of objects.

38. A method for operating an optical sensor system for a touchless measurement according to claim 1, wherein light is projected to at least one illumination position, the at least one illumination position is imaged reflected by the surface of the liquid on at least one photo detector, wherein light is projected simultaneously to plural illumination positions and/or light is projected under different angles to the same illumination position and/or the at least one illumination position is imaged on plural photo detectors, the vertical distance between the at least one illumination position and the interface is varied, the maximum value of the measurement signal of at least one photo detector is acquired when the vertical distance is varied, and the position of the illumination position at the maximum value of the measurement signal is determined as the position of the interface.

39. A method according to claim 38, wherein in the event that no maximum value of the measurement signal of at least one photo detector is detected when the vertical distance between illumination position and interface is varied, and thereafter is searched anew for a maximum value of the measurement signal through variation of the vertical distance of the at least one illumination position and the interface, the position of the at least one illumination position is varied in the direction transverse to the vertical.

40. A method for operating an optical sensor system according to claim 1, wherein light in the direction of an interface is projected to at least one illumination position, the distribution of the reflected quantity of light is detected by means of plural photo detectors, and the probable position of the optimum reflexion position on the interface and/or the probable position and/or the identity of the interface is determined on the basis of the detected distribution of the quantity of light.

41. A method according to claim 39, wherein the at least one illumination position is adjusted to the probable position of the optimum reflexion position and/or the probable position of the interface, and than the measurement is repeated.

42. A method for operating an optical sensor system according to claim 1, wherein light is projected to plural illumination positions, the illumination positions are moved across an interface, each illumination position is imaged on a photo detector assigned to the same, and the measurement signals supplied by the plural photo detectors are compared and a measurement error is stated in the case of a deviation.

43. A method according to claim 38, wherein the determined positions and/or identities of interfaces and/or objects are memorised and/or are used for controlling and/or examining a process to for treating liquids.

44. A method according to claim 38, wherein positions and/or identities of interfaces and/or objects are detected in the beginning of a process for treating liquids and/or are detected anew in the course of a process for treating liquids and/or changes of the conditions through the process for treating liquids are calculated on the basis of the detected positions and/or identities.

45. A method according to claim 44, wherein the calculated values are checked by a new detection.

46. A method according to claim 44, wherein the detected and/or calculated positions and/or identities are filed and/or displayed.

47. The optical sensor system of claim 1 wherein the at least one photo detector (13) is plural photo detectors (13) and the analyzing unit (21) is connected to the plural photo detectors (13) for analyzing the at least one measurement signal.

48. An optical sensor system for touchless measurement on an apparatus for treating liquids, with a device for projecting light (9, 10, 11) to at least one illumination position (12) in space, at least one device for imaging (11,) the at least one illumination position reflected by the surface of a liquid on at least one photo detector (13) in order to supply at least one measurement signal depending on the received light, wherein the device for projecting (9, 10, 11) is a device for simultaneously projecting light under different angles to the same illumination position (12) and an analyzing unit (21) connected to the at least one photo detector (13) for analyzing the at least one measurement signal.

49. The optical sensor system of claim 48 wherein the at least one photo detector (13) is plural photo detectors (13) and the analyzing unit (21) is connected to the plural photo detectors (13) for analyzing the at least one measurement signal.

* * * * *